US010214695B2

(12) United States Patent
King et al.

(10) Patent No.: US 10,214,695 B2
(45) Date of Patent: Feb. 26, 2019

(54) PROCESS FOR RECOVERING HEAT FROM A HYDROCARBON SEPARATION

(71) Applicant: UOP LLC, Des Plaines, IL (US)

(72) Inventors: Stephen T. King, Villa Park, IL (US); Adam J. Kanyuh, Streamwood, IL (US); Xin X. Zhu, Long Grove, IL (US)

(73) Assignee: UOP LLC, Des Plaines, IL (US)

( * ) Notice: Subject to any disclaimer, the term of this patent is extended or adjusted under 35 U.S.C. 154(b) by 687 days.

(21) Appl. No.: 14/445,512

(22) Filed: Jul. 29, 2014

(65) Prior Publication Data

US 2015/0101921 A1 Apr. 16, 2015

Related U.S. Application Data

(60) Provisional application No. 61/891,497, filed on Oct. 6, 2013.

(51) Int. Cl.
 | | |
 |---|---|
 | *C07C 7/04* | (2006.01) |
 | *C07C 7/00* | (2006.01) |
 | *B01D 3/14* | (2006.01) |
 | *B01D 1/28* | (2006.01) |
 | *C10G 53/02* | (2006.01) |
 | *C10G 7/00* | (2006.01) |
 | *B01D 5/00* | (2006.01) |

(52) U.S. Cl.
CPC ........... *C10G 53/02* (2013.01); *B01D 1/2856* (2013.01); *C10G 7/00* (2013.01); *B01D 1/28* (2013.01); *B01D 3/14* (2013.01); *B01D 3/143* (2013.01); *B01D 3/148* (2013.01); *B01D 5/0039* (2013.01); *C07C 7/00* (2013.01); *C07C 7/04* (2013.01); *Y02P 70/34* (2015.11)

(58) Field of Classification Search
CPC ........ B01D 3/143; B01D 5/0039; B01D 1/28; B01D 3/14; B01D 3/148; B01D 1/2806; B01D 1/2843; B01D 1/2856; C07C 7/04
See application file for complete search history.

(56) References Cited

U.S. PATENT DOCUMENTS 4,559,108 A * 12/1985 Ahlberg ............... B01D 1/2806
 202/154
4,753,667 A 6/1988 O'Connell et al.
(Continued)

OTHER PUBLICATIONS

"Compressors and Silent Root Causes for Failure", Feb. 21, 2009 (date obtained from Wayback Machine), Available online at http://www.barringer1.com/dec08prb.htm.*
(Continued)

*Primary Examiner* — Jonathan Miller
*Assistant Examiner* — Jonathan Luke Pilcher

(57) ABSTRACT

A process for recovering heat from the separation of hydrocarbons. The overhead vapor stream from a fractionation column is passed to a two stage heat pump compressor. The first stage of compression is used to reboil the fractionation column. The second stage is compressed and cooled passed to a separation zone. The liquid in the separation zone may be passed back to the fractionation column as secondary reflux, and/or recovered as liquid product. Heat may also be removed from the second stage. A suction drum on the first stage may be used to protect the heat pump compressor from any droplets in the overhead stream.

17 Claims, 2 Drawing Sheets

(56) References Cited

U.S. PATENT DOCUMENTS

Figure 1:
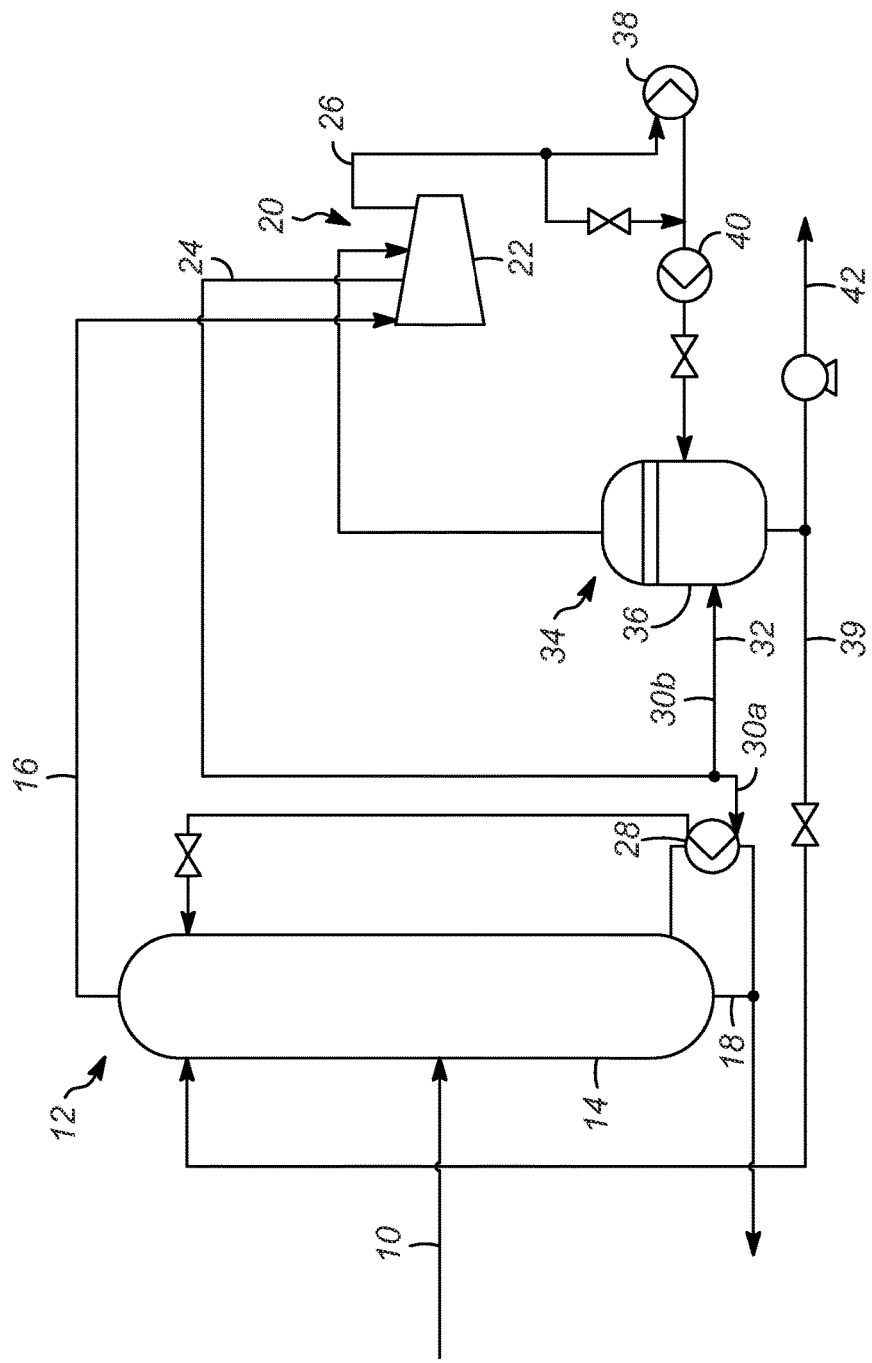

| | | | | |
|---|---|---|---|---|
| 5,678,424 | A * | 10/1997 | Nazar | C07C 7/04 62/630 |
| 6,584,803 | B2 * | 7/2003 | Oakey | C07C 7/04 62/621 |
| 6,609,393 | B2 * | 8/2003 | Oakey | C07C 7/04 62/620 |
| 6,637,239 | B2 * | 10/2003 | Oakey | C07C 7/04 62/620 |
| 6,837,071 | B2 * | 1/2005 | Oakey | F25J 3/0209 62/631 |
| 7,842,847 | B2 | 11/2010 | Panditrao et al. | |
| 7,981,256 | B2 | 7/2011 | Wegerer et al. | |
| 8,323,457 | B2 * | 12/2012 | Townsend | B01D 3/007 202/153 |
| 8,349,263 | B2 | 1/2013 | Panditrao et al. | |
| 2006/0006054 | A1 * | 1/2006 | Gobbel | C07D 301/32 203/24 |
| 2009/0120780 | A1 * | 5/2009 | Wegerer | B01D 3/14 203/87 |
| 2010/0108487 | A1 * | 5/2010 | Townsend | B01D 3/007 203/26 |
| 2013/0131417 | A1 | 5/2013 | Werba et al. | |
| 2013/0267751 | A1 * | 10/2013 | Favilli | B01D 1/28 585/806 |

OTHER PUBLICATIONS

Annakou et al., "Rigorous investigation of heat pump assisted distillation," Heat Recovery Systems & CHP (1995), 15(3), 241-247.

Olujic et al., "Conceptual design of an internally heat integrated propylene-propane splitter," Energy (2006), 31(15), 3038-3096.

Chen et al., "Evaluation and comparison of internal/external heat integration configurations . . . " Conference Proceedings—AIChE Spring Meeting & 9th Global Congress . . . (2013).

* cited by examiner

PROCESS FOR RECOVERING HEAT FROM A HYDROCARBON SEPARATION

RELATED APPLICATIONS

This application claims priority to U.S. Provisional Application No. 61/891,497 filed on Oct. 16, 2013, the entirety of which is incorporated herein.

FIELD OF THE INVENTION

This invention relates generally to a process for recovering heat from a hydrocarbon separation process.

BACKGROUND OF THE INVENTION

Petroleum refining and petrochemical processes frequently involve separating hydrocarbon components that have very similar structure and properties.

For example, propylene-propane splitters typically comprise distillation towers that are used to separate $C_3$ streams into polymer grade propylene (PGP) in a net overhead and propane in a net bottoms. Due to the low relative volatility of propylene and propane, typically a very large tower with 150 to 250 trays is used. Additionally, the tower also typically includes a reflux to feed ratio of 5 to 10. Since the relative volatility of propylene and propane is so low (typically 1.05 to 1.20), the energy required to separate propylene and propane into high purity component streams is very high.

Typically, a heat pump compressor is utilized to condense (or remove energy) in the fractionation column overhead and re-boil (or feed energy) into the column bottoms because the vapor pressure of propylene and propane are similar and the heat removed from the column overhead for condensing can be transferred or pumped to the tower bottoms for re-boiling.

In a traditional design, such as the design disclosed in U.S. Pat. Pub. No. 2013/0131417, which is assigned to the assignee of the present invention, and the entirety of which is incorporated herein by reference, an overhead vapor from a propylene-propane splitter column ("PP Splitter") is sent to the first stage heat pump compressor. In the first stage heat pump compressor, the vapor is compressed to the required pressure, typically between approximately 1034 to 1724 kPag (150 to 250 psig), which is the minimum temperature for a heat exchanger to condense vapor on the hot side and re-boil liquid on the cold side of the heat exchanger. The duty required to re-boil the PP Splitter determines the vapor flow rate to the re-boiler/condensers. Since the condensing duty is greater than the re-boiling duty of PP Splitter, there is extra vapor from the first stage discharge that requires heat removal. This extra vapor is sent to the second stage of the heat pump compressor, where it can be compressed to a pressure able to be condensed by another heat exchanger at a warmer temperature. Subsequently, this stream is flashed across a valve into a suction drum down to the column overhead pressure to provide Joule-Thomson effect cooling to the column overhead and accumulate propylene liquid product in the suction drum.

In such a system described above, when the second stage discharge stream is flashed down to the column overhead pressure, the resulting vapor from this flash is then re-processed in the heat pump first stage and second stages, sequentially. Thus, the first stage of the heat pump compressor, which is the larger capacity stage requiring more utility, needs to process the column overhead vapor along with the vapor from the second stage discharge flash, thereby increasing the overall capacity and utility requirement of the compressor.

It would be desirable to have a process which improves on the efficiency and heat recovery on such a process.

SUMMARY OF THE INVENTION

A process which allows more efficient heat recovery has been discovered.

In one aspect, the present invention may be characterized as a process for separating hydrocarbons and recovering heat which includes: separating a feed stream comprising hydrocarbons in a first separation zone into an overhead stream and a bottoms stream; the overhead steam being a vapor stream and the bottom stream being a liquid stream; passing at least a portion of the overhead stream to a compression zone, the compression zone configured to produce a first output stream and a second output stream; transferring heat from at least a portion of the first output stream of the compression zone to the first separation zone; removing heat from the second output stream of the compression zone; and, passing the second output stream of the compression zone to a second separation zone, wherein the second separation zone has a pressure higher than a pressure of the overhead stream.

In at least one embodiment the first separation zone is a fractionation column.

In some embodiments, the process further includes recovering a liquid stream from the second separation zone.

In some embodiments, the process also includes passing at least a first portion of the first output stream of the compression zone to the first separation zone after transferring heat from the first portion of the first output stream. It is further contemplated that the process includes passing a second portion of the first output stream of the compression zone to the second separation zone. It is also contemplated the first portion of the first output stream of the compression zone comprises between approximately 75% to 90% by volume of the first output stream of the compression zone.

It at least one embodiment, the second separation zone provides an overhead stream and a bottoms stream. The process further includes passing the overhead stream to the compression zone.

In some embodiments, the process further includes recovering liquid from the overhead stream of the first separation zone prior to passing the overhead stream to the compression zone. It is further contemplated that process also includes recovering liquid from the overhead stream of the first separation zone in a third separation zone. The third separation zone is preferably disposed between the first separation zone and the compression zone.

In still other embodiments, the process includes cooling the second output stream of the compression zone in a cooling zone after removing heat from the second output stream and before the second output stream is passed to the second separation zone.

In another aspect, the present invention may be characterized as a process for separating hydrocarbons and recovering heat which includes: separating a feed stream comprising hydrocarbons in a first separation zone into an overhead stream and a bottoms stream; separating the overhead stream from the first separation zone into a vapor stream and a liquid stream; passing the vapor stream to a compression zone, the compression zone configured to produce a first output stream and a second output stream; removing heat from the first output stream of the compression zone; condensing and recycling the first output stream of the compression zone to the first separation zone; recovering heat from the second output stream of the compression zone; and, passing the second output stream of the compression zone to a second separation zone. The second separation zone is configured such that any vapor in the second separation zone is from the compression zone.

In some embodiments, the process includes passing a portion of the first output stream of the compression zone to the second separation zone prior to recovering heat from the first output stream. It is contemplated that the portion of the first output stream passed to the second separation zone comprises between approximately 10-25% by volume of the first output stream.

In at least one embodiment, the process includes cooling the second output stream of the compression zone in a cooling zone after removing heat from the second output stream and before the second output stream is passed to the second separation zone.

In yet another embodiment, the second separation zone provides an overhead stream and a bottoms stream. The process may include passing the overhead stream to the compression zone.

In some embodiment, the process includes recovering a liquid stream from the second separation zone.

In still other embodiments, the overhead stream from the first separation zone is separated into a vapor stream and a liquid stream in a third separation zone. It is contemplated that the third separation zone is disposed between the first separation zone and the compression zone. It is further contemplated that the first separation zone comprises a distillation column. It is also contemplated that a pressure in the third separation zone is lower than in a pressure in the second separation zone.

Additional objects, embodiments, and details of the invention are set forth in the following detailed description of the invention.

DETAILED DESCRIPTION OF THE DRAWINGS

Figure 2:
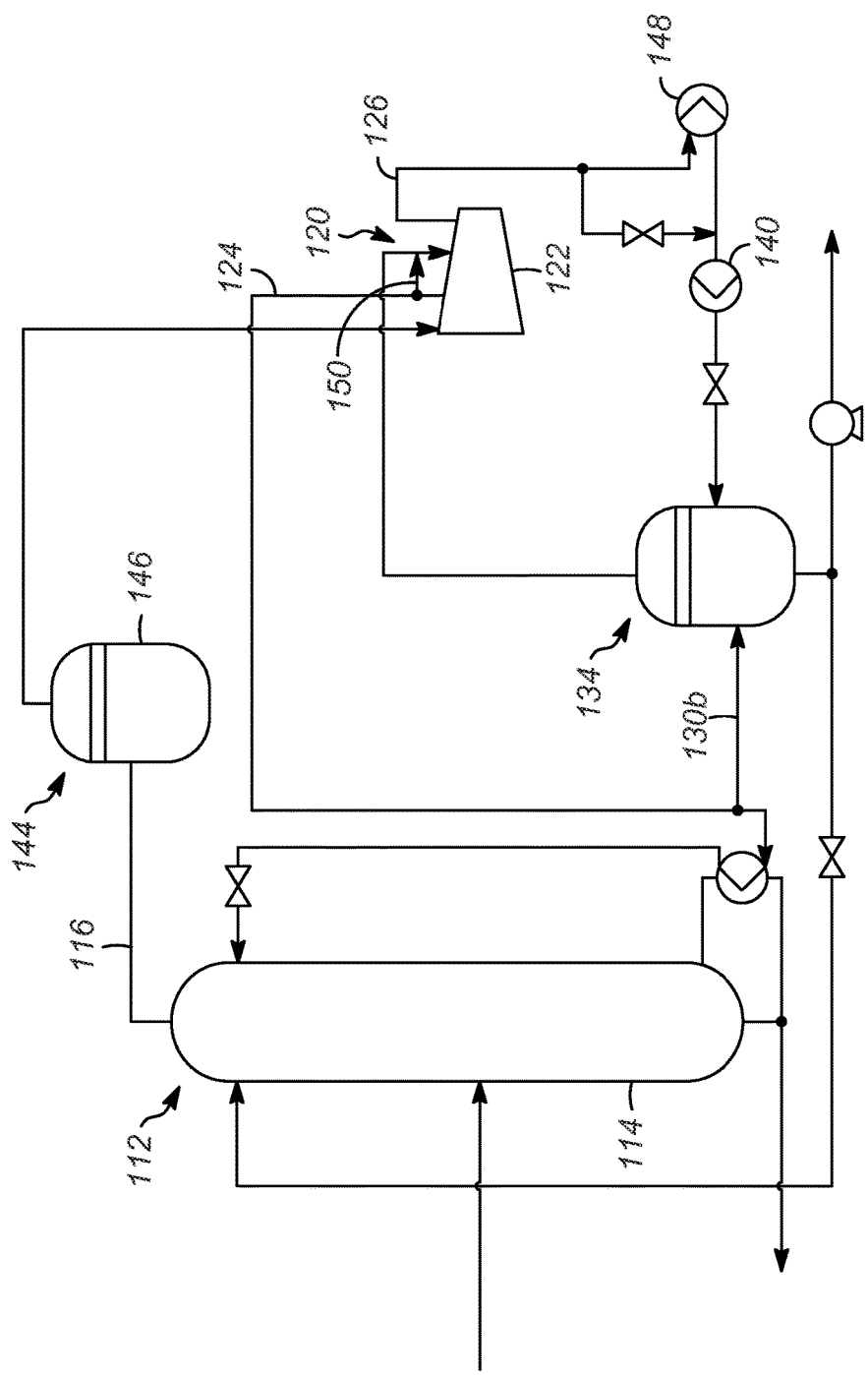

The drawings are simplified process diagrams in which:

FIG. 1 shows a process flow diagram of a process according to one or more embodiments of the present invention; and, FIG. 2 shows another process flow diagram of a process according to one or more embodiments of the present invention.

DETAILED DESCRIPTION OF THE INVENTION

A method has been developed which allows for a more efficient separation of various hydrocarbons by increasing the heat recovery from same.

In the various processes of the invention, the first and second stages of the heat pump compressor are decoupled so that the first stage is processing the vapor from the column overhead and the second stage is processing only the material needed to remove the excess condensing energy needed for the column operation.

In some embodiments, a utility benefit over the current heat pump design can be realized from the reduction of the first stage suction volumetric flow because now the first stage is only processing column overhead vapor (instead of additional vapor from the second stage flash).

Additionally, processes according to the present invention will allow for cooler second stage suction temperature since the vapor/liquid re-contacting occurs in a second stage suction drum and cools the suction gas to the second stage. The higher density gas reduces compressor size and utility by lowering the required compressor head.

Furthermore, in some embodiments, a pump used to send a reflux back to the column is eliminated because the second stage suction drum liquid operates at a higher pressure and the secondary reflux can be pressured back to the column overhead as liquid. Additionally, a secondary reflux line from a suction drum may be eliminated since the total reflux may be combine at grade. In the present invention, the density of the primary and secondary reflux material will be similar. In a traditional scheme, the reflux pump sub-cooled the secondary reflux. The primary reflux being bubble point material had a lower density than the secondary reflux material and the primary and secondary reflux lines were typically sent up the tower independently. Combining the primary reflux with the secondary sub-cooled reflux will increase the static head in the overall reflux line and increase the first stage utility. These and other benefits will be appreciated in view of the follow description of some of the embodiments of the present invention.

With reference to FIG. 1, an embodiment of the present invention will be described. As shown, a feed stream 10 comprising hydrocarbons to be separated is passed to a first separation zone 12. In a preferred embodiment, the first separation zone 12 comprises one or more fractionation columns 14 for separating hydrocarbons, for example, isobutane and normal butane, isobutylene and isobutene, or propane and propylene. In a most preferred embodiment, the one or more fractionation columns 14 comprises a propylene-propane splitter column.

The one or more fractionation columns 14 are operated under conditions to separate the hydrocarbons in the feed stream 10 into an overhead vapor stream 16 and a bottoms stream 18. In at least one embodiment, the one or more fractionation columns 14 are each operated with an overhead pressure of approximately 689 kPag (100 psig). In the case of a propylene-propane splitter column, the bottoms stream 18 may comprise propane as well as other heavier hydrocarbons which may be passed to other zones or units for further separation and processing.

The overhead vapor stream 16 from the first separation zone 12 is passed to a compression zone 20. In a most preferred embodiment, the compression zone 20 comprises a heat pump compressor 22 that produces two output (or discharge) streams, a first stage output stream 24 and a second stage output stream 26. The heat pump compressor 22 will compress the overhead vapor stream 16 from the first separation zone 12 up to between approximately 1034 to 1724 kPag (150 to 250 psig) to form the first stage output stream 24. The pressure of the first stage output stream 24 is based upon the required heat exchanger minimum approach temperature that will re-boil the bottoms stream 18 of the first separation zone 12 and fully condense the vapor of the first stage output stream 24 to form primary liquid reflux (discussed below).

In one or more embodiments, the first stage output stream 24 will be split into two portions 30a, 30b with approximately 75 to 90% (the first portion 30a) being passed a heat exchanger 28 to transfer heat (or heat pump) from the overhead vapor stream 16 of the first separation zone 12 to the bottoms stream 18 of the first separation zone 12. Accordingly, the heat from the hot side of the heat exchanger 28 transfers to the cold side and serves as the heat source to re-boil the first separation zone 12.

The heat exchanger 28 may be a thermosyphion system in which a cold side outlet temperature is approximately the same as the temperature of the bottoms stream 18 of the first separation zone 12. The heat exchanger 28, as well as other heat exchangers discussed herein, may be also of any conventional design, with one example being a cross-flow tube-in-shell design and another example using high heat transfer technologies such as Highflux™ (available from UOP, Des Plaines, Ill.) or plate type exchangers.

The vapor in the hot side outlet of the heat exchanger 28 fully condenses and is passed back to the first separation zone 12 as primary reflux material. The outlet of the heat exchanger 28 may include a 34 to 172 kPa (5 to 25 psi) pressure drop for controlling the flow of the first stage output stream 24 back to the first separation zone 12.

As mentioned above, in some embodiments of the present invention, the first stage output stream 24 is split into two portions 30a, 30b. The second portion 30b of the first stage output stream 24 (preferably the remaining 10 to 25%) may bypass the heat exchanger 28 and be passed via a bypass line 32 to a second separation zone 34. Preferably, the second separation zone 34 comprises a suction drum 36 having an operating pressure of approximately 1,241 kPag (180 psig).

As the second portion 30b of the first stage output stream 24 enters the second separation zone 34, it will contact with the second stage output stream 26. The second separation zone 34 allows the vapor in the first stage output 24 and liquid from the second stage output 26 to contact and disengage, which cools the second stage output stream 26 before it is compressed in the second stage of the heat pump compressor 22. The lower temperature allows for a higher density of gas to enter the second stage of the heat pump compressor 22. This will reduce the compressor head and utility for the second stage.

In order to produce the second stage output stream 26, the heat pump compressor 22 compresses the remaining vapor from the first separation zone 12 with the flash vapor from second stage output stream 26 in the second separation zone 34. The pressure of the second stage output stream 26 is preferably approximately 2,689 kPag (390 psig) to condense vapor in process exchanger 38 followed by an air or water cooled trim cooler 40. The air or water cooled trim cooler 40 removes excess heat from the second stage output stream 26 which is flashed back to the second separation zone 34 to be recompressed in the second stage of the heat pump compressor 22 again.

Liquid from the second separation zone 34 may be passed back to the fractionation column 14 via a line 39 due to the pressure differential between the second separation zone 34 and the overhead of the first fractionation column 14. Also, a net overhead liquid 42 may be pumped to pressurized storage. In embodiments in which the fractionation column 14 comprises a PP Splitter, the net overhead liquid 42 typically polymer grade propylene.

Another embodiment of the present invention is shown in FIG. 2, in which the overhead vapor 116 from the first separation zone 112 is passed to a third separation zone 144 before passing to the compression zone 120. In the third separation zone 144, any droplets in the overhead vapor 116 that may have condensed from ambient heat loss may be separated out. In a preferred embodiment, the third separation zone 144 comprises a suction drum 146. Liquid in the third separation zone 144 is not expected to accumulate if the process is near adiabatic. Any liquid in the third separation zone 144 may be re-vaporized with hot vapor in the overhead vapor 116. Alternatively, the liquid from the third separation zone 144 can be pumped intermittently with a low capacity pump to the second separation zone 134. In an alternative embodiment, a mesh blanket may be used (not shown), for example, in the top of the fractionation column 114, to allow for droplets in the vapor at the top of the fractionation column 114 to accumulate instead of being passed to the heat pump compressor 122. In this case, the suction drum 146 would not be required since the third separation zone 144 would be integrated into the fractionator overhead. The third separation zone 144 and mesh blanket are used to protect the heat pump compressor 122 from receiving minimal liquid, as the liquid can damage the heat pump compressor 122. Other designs to protect the heat pump compressor 122 may also be utilized.

Additionally, as shown in FIG. 2, in this embodiment of the present invention, the second stage output stream 126 is passed to a heat recovery process exchanger 148 before passing through a trim cooler 140 and into the second separation zone 134. Any heat recovered in the heat recovery process exchanger 148 can be used in other processes in refining plant.

Finally, in FIG. 2, a portion of the first stage output 124 may be passed back directly to the heat pump compressor 122 for use as a second stage inlet (or suction) to be compressed into the second stage output (or discharge) stream 126 via a line 150. In this case, the line 130b from the first stage output 124 to the second separation zone 134 would not be required.

The remaining elements of this embodiment in FIG. 2 are similar to the first embodiment, shown in FIG. 1, and therefore the description of same above is incorporated herein.

It is estimated that processes according to one or more embodiments of the present invention can provide a capital expenditure savings of at least $2 million dollars as well as a yearly utility expenditure savings of over $1 million dollars. Thus, not only do the process provide for more efficient heat recovery, the processes do so with a savings on the capital required to implement the processes.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understating the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for separating hydrocarbons and recovering heat from a stream, the process comprising:

separating a feed stream comprising hydrocarbons in a first separation zone into an overhead stream and a bottoms stream, the overhead stream being a vapor stream and the bottom stream being a liquid stream;

passing at least a portion of the overhead stream to a compressor configured to produce a first output stream and a second output stream, wherein the second output stream has a greater pressure than the first output stream;

transferring heat from at least a first portion of the first output stream of the compressor to the first separation zone and then passing the first portion of the first output stream of the compressor to the first separation zone;

passing a second portion of the first output stream of the compressor to a second separation zone;

removing heat from the second output stream of the compressor; and, passing the second output stream of the compressor to the second separation zone, wherein the second output stream of the compressor is cooled by contact cooling with the second portion of the first output stream of the compressor, the second separation zone has a pressure higher than a pressure of the overhead stream, and the second separation zone is configured such that any vapor in the second separation zone is from the compressor.

2. The process of claim 1, wherein the first separation zone is a fractionation column.

3. The process of claim 1 further comprising: recovering a liquid stream from the second separation zone.

4. The process of claim 1 wherein the first portion of the first output stream of the compressor comprises between approximately 75% to 90% by volume of the first output stream of the compressor.

5. The process of claim 1 wherein the second separation zone provides an overhead stream and a bottoms stream, and the process further comprising:

passing the overhead stream to the compressor.

6. The process of claim 1 further comprising:

recovering liquid from the overhead stream of the first separation zone prior to passing the overhead stream to the compressor.

7. The process of claim 6 further comprising:

recovering liquid from the overhead stream of the first separation zone in a third separation zone, the third separation zone being disposed between the first separation zone and the compressor.

8. The process of claim 1 further comprising:

cooling the second output stream of the compressor in a cooling zone after removing heat from the second output stream and before the second output stream is passed to the second separation zone.

9. A process for separating hydrocarbons and recovering heat, the process comprising:

separating a feed stream comprising hydrocarbons in a first separation zone into an overhead stream and a bottoms stream;

separating the overhead stream from the first separation zone into a vapor stream and a liquid stream;

passing the vapor stream to a compressor configured to produce a first output stream and a second output stream, wherein the second output stream has a greater pressure than the first output stream;

passing a first portion of the first output stream of the compressor to a second separation zone;

recovering heat from a second portion the first output stream of the compressor;

condensing and recycling the second portion of the first output stream of the compressor to the first separation zone;

removing heat from the second output stream of the compressor; and, passing the second output stream of the compressor to the second separation zone, wherein the second output stream of the compressor is cooled by contact cooling with the portion of the first output stream of the compressor and the second separation zone is configured such that any vapor in the second separation zone is from the compressor.

10. The process of claim 9, wherein the first portion of the first output stream passed to the second separation zone comprises between approximately 10-25% by volume of the first output stream.

11. The process of claim 9 further comprising:

cooling the second output stream of the compressor in a cooling zone after removing heat from the second output stream and before the second output stream is passed to the second separation zone.

12. The process of claim 9 wherein the second separation zone provides an overhead stream and a bottoms stream, and further comprising:

passing the overhead stream to the compressor.

13. The process of claim 9 further comprising: recovering a liquid stream from the second separation zone.

14. The process of claim 9 wherein the overhead stream from the first separation zone is separated into a vapor stream and a liquid stream in a third separation zone.

15. The process of claim 14 wherein the third separation zone is disposed between the first separation zone and the compressor.

16. The process of claim 15 wherein the first separation zone comprises a distillation column.

17. The process of claim 16 wherein a pressure in the third separation zone is lower than in a pressure in the second separation zone.

* * * * *